(12) United States Patent
Schnittger et al.

(10) Patent No.: US 7,211,249 B2
(45) Date of Patent: May 1, 2007

(54) HEAT-GENERATING COMPOSITION FOR TOPICAL APPLICATION TO SKIN

(75) Inventors: Steven F. Schnittger, Huntington Station, NY (US); Denise M. DiCanio, Centereach, NY (US); Peter J. Lentini, Bayside, NY (US)

(73) Assignee: Color Access, Inc., Melville, NY (US)

( * ) Notice: Subject to any disclaimer, the term of this patent is extended or adjusted under 35 U.S.C. 154(b) by 430 days.

(21) Appl. No.: 10/390,415

(22) Filed: Mar. 17, 2003

(65) Prior Publication Data

US 2004/0185023 A1     Sep. 23, 2004

(51) Int. Cl.
*A61K 38/44* (2006.01)
*A61K 8/02* (2006.01)
*A61K 8/11* (2006.01)
*A61K 9/50* (2006.01)
*A61Q 19/00* (2006.01)
*C12N 11/04* (2006.01)
*C12N 9/02* (2006.01)

(52) U.S. Cl. ............... 424/94.4; 424/401; 424/490; 435/182; 435/189

(58) Field of Classification Search .............. None
See application file for complete search history.

(56) References Cited

U.S. PATENT DOCUMENTS

| | | | |
|---|---|---|---|
| 2,635,069 A | 4/1953 | Baker | |
| 5,360,732 A | 11/1994 | Berka et al. | |
| 5,395,620 A | 3/1995 | Huc et al. | |
| 5,811,114 A | 9/1998 | Knight et al. | |
| 6,752,998 B2 | 6/2004 | Verdrel-Lahaxe et al. | |
| 2003/0101984 A1 | 6/2003 | Li et al. | |
| 2004/0028711 A1 | 2/2004 | Uchida et al. | |

FOREIGN PATENT DOCUMENTS

| | | |
|---|---|---|
| EP | 1 050 313 | 11/2000 |
| WO | WO 01/19331 | 3/2001 |

OTHER PUBLICATIONS

Product literature for Agera, Catalyse Enzyme Gel, Biosyn, Inc., Harahan, LA (Mar. 12, 2003).

CTFA On-Line, http://www.ctfa.org, (Jul. 14, 2006), homepage, frontpage, and entries in Ingredient Database (Dictionary/Handbook) for Hydrated Silica, Kaolin, and Alumina, 7pp.

*Primary Examiner*—David M. Naff
(74) *Attorney, Agent, or Firm*—Peter Giancana

(57) ABSTRACT

The present invention provides a method of sustaining the rate of heat felt on the skin as a result of an exothermic reaction between a combination of an unencapsulated and an encapsulated catalase, and peroxide. The catalase component provides a sustained heat release and in combination with other non-catalase heat-generating agents, the rate of heat released and felt on the skin can be further controlled. The compositions of the present invention also soften the skin and contribute to the health of the skin by reducing the presence of oxygen free radicals on the skin surface.

9 Claims, No Drawings

HEAT-GENERATING COMPOSITION FOR TOPICAL APPLICATION TO SKIN

FIELD OF THE INVENTION

The present invention relates to cosmetic compositions containing a catalase-based system to manipulate heat generated by an exothermic reaction. More specifically, the invention relates to compositions containing an encapsulated catalase enzyme and other heat-generating agents to sustain the release of heat and the sensation of heat on the skin surface after topical application.

BACKGROUND OF THE INVENTION

Heat-producing compositions are desirable because they feel warm and pleasant sensation on the skin. The warm feeling is typically more appealing than compositions that feel cold when applied to the body and facial skin. This is particularly, the case when using massage products on the body. The relaxation and enjoyment of a massage is rudely interrupted by the anticipation and shock of a cold product being applied to the body, having a normal body temperature. In addition, hair products and hand cleansers can be used with cold water while feeling warmer than the temperature of the water. These products can be warmed in a heated water bath, however, the application of heat to the product may cause degradation of the product by, for example, the occurrence of phase separation, or the breakdown of the active ingredients contained in the product. In addition, the process of heating the product takes time and requires the use of extra equipment such as the water bath.

Another method for creating a warm sensation on the skin is the use of a heat generating agent. Examples of some known heat generating agents in the art, include, but are not limited to, zeolite, iron powders, silica gel, and activated alumina. Another known method of generating heat is to intrinsically establish, within the product, the conditions for an exothermic reaction based on the conversion of hydrogen peroxide to water and oxygen by a catalase. As disclosed in EP 1,050,313, the hot system based on the use of catalase is a type of disinfectant and cleanser used for contact lenses. Catalase is widely distributed in nature and is found in various quantities in virtually all humans and animal tissues. Its use in medicine, however, has been limited due to stability problems. Catalase is known to degrade when subjected to heat as well as being sensitive to low temperatures. Further, catalase is extremely sensitive to light. These problems threaten the stability of catalase regardless of whether it is in solution or stored as a solid. Skin care compositions are also known and are described in WO 01/19331. However, the catalase is not used in a system for creating heat but rather to treat and cleanse skin that has been exposed to solar radiation.

Catalase can be derived from both animal and non-mammalian sources. Bovine catalase is not as active, however, as some other sources such as for example catalase obtained from molds. In particular, U.S. Pat. Nos. 2,635,069 and 5,360,732 disclose catalase obtained from *Aspergillus niger*. The catalase is prepared by conventional methods of fermenting microorganisms, breaking cell bodies, and purifying the crude extract. It is also known to combine a stabilized gel of the enzyme catalase with hydrogen peroxide to produce oxygen and water on the skin for oxygenation. For example, according to product information published by Agera®, a product by the name of Catalyse Enzyme Gel is to be combined with another product by the name of Aerobic Infusion to provide a boost of oxygen and to soften the skin. In addition, although it is known to encapsulate actives, it is not known in the prior art to use a non-mammalian derived catalase that is encapsulated nor has the prior art recognized the ability to sustain heat achieved as a result of encapsulating the catalase.

It is likewise not known to combine the encapsulated catalase with free catalase and other known heat generating agents in a heat generating system to manipulate and control the rate of heat generated. Typically, regardless of the heat generating agent employed, heat is released such that the intensity of heat is constant during the exothermic reaction. The change in temperature over time on the skin is relatively small, and it is harder for the skin to sense the heat over time because there is little heat. Further, to reproduce the heat, conditions for another subsequent exothermic reaction have to be prepared. Thus, re-application of the entire product is necessary to sustain the warm feeling on the skin. However, the sensitivity of the skin to the heat is diminished and the sensation of heat is less effective. Therefore, there is a need for a product that works with the sensitivity of the skin to heat to provide a sensation of heat in a smooth continuous rate on the skin. The present invention introduces the concept of a sustained heat release such that a temperature-time curve is produced and heat is more easily sensed on the surface of the skin and is substantially non-irritating.

SUMMARY OF THE INVENTION

The invention relates to a composition comprising a heat-generating effective amount of a catalase component of at least one unencapsulated heat-generating agent and at least one encapsulated catalase, and a peroxide component that react when combined together to produce heat. The two reactive components generate a sustained release of beat by an exothermic reaction whereby, in general, peroxide is converted to water and oxygen. The unencapsulated heat-generating agent can be a catalase agent that also undergoes the exothermic reaction when combined with the peroxide component. The rate of heat released exhibits a negative change in temperature (° C.) in comparison with free catalase alone or other non-catalase based heat-generating agents alone. The catalase component may be combined with other complementary non-catalase agents especially those that are water sorbing based agents (i.e., agents that are capable of sorbing water exothermically) for extending the duration of time that heat is released. The non-catalase agent can be encapsulated or unencapsulated.

In addition, the present invention includes methods of topically applying the components of the composition to the skin to produce the exothermic reaction and thus, the sustained heat curve and heat sensation on the skin. The methods of the present invention also include softening the skin, oxygenating the skin and protecting the skin from damage to the barrier function caused by the presence of free radicals. The compositions of the present invention are contained in a unitary package for dispensing the topically applied compositions in a substantially simultaneous fashion. The package contains at least two separate, non-communicating chambers for at least each of the two different reactive components, namely, the catalase component and the peroxide component. Each of the chambers holds a different reactive component, and has an opening for dispensing each of the components such that they react with each other when they are commingled upon dispensing or as separate flow streams, but which remain inert while they are contained in the separate chambers.

DETAILED DESCRIPTION OF THE INVENTION

The present invention, in its various embodiments, is predicated on the surprising discovery that heat-generating effective amounts of a catalase component comprising at least one encapsulated catalase that when topically applied to the skin in combination with a peroxide component undergoes a protracted decrease in temperature for a period of about 3 minutes after the composition is applied to the skin (i.e., a controlled release of heat), and exhibits beneficial effects on the skin. As used herein the term "controlled" or "sustained" release in the context of the present specification means that heat is generated or released by an exothermic reaction whereby peroxide is converted to water and oxygen at a rate such that the percent difference per minute in temperature, as measured in ° C., is negative for each of the first 3 minutes. In addition, the percent difference in temperature per minute as measured in ° C. after topically applying the compositions of the present invention on the skin over a period of about 5 minutes preferably negative for each of the first two minutes, and more preferably negative for the first minute. The initial temperature generated by the compositions of the present invention, measured after 30 seconds, is greater than about 35° C., and the average percent difference in temperature over a period of 5 minutes is greater than 2, preferably greater than 3, and more preferably greater than 4.

Any form of catalase derived from animal tissues, plants, or microorganisms can be used in the catalase component of the present invention. Thus, the catalase can be derived from, for example, micrococcus varians or fungus. A fungal catalase is preferably *Aspergillus niger* (*A. niger*) catalase. Catalases [hydrogen peroxide: hydrogen peroxide oxidoreductases (EC 1.11.1.6)] are enzymes which catalyze the conversion of 2 molecules of hydrogen peroxide ($H_2O_2$) to one molecule of oxygen ($O_2$) and 2 molecules of water ($H_2O$). Catalase enzymes are ubiquitous and nearly all forms of catalase are known to be characterized by four polypeptide subunits, each having a molecular weight of about 50,000 to 60,000 and containing one protohemin prosthetic group per subunit. Production of *A. niger* catalase-R, for example, is reported in U.S. Pat. No. 5,360,732, the contents of which are incorporated herein by reference. Although catalases from filamentous fungi share a similar subunit number and heme content, fungal catalases have several characteristics that distinguish them from mammalian-based catalases, such as bovine catalase. Fungal catalases have subunit molecular weights ranging from 80,000 to 97,000, and are therefore, substantially larger molecules than catalases from other organisms. Further, fungal catalases such as *A. niger* are more stable than bovine catalase to proteolysis and to inactivation by glutaraldehyde, SDS, and have lower affinity for catalase inhibitors. The *A. niger* catalase is stable even when subjected to the extremes of pH, hydrogen peroxide, and temperature. The difference in stability between fungal catalase and bovine catalase is most likely due to the differences in structural characteristic and composition of the proteins. The tradeoff with fungal catalase in comparison with bovine catalase is that its rate of deactivation in hydrogen peroxide has been found to be at least an order of magnitude lower for *A. niger* catalase than for bovine catalase.

Catalase preparations from *A. niger* are available commercially for diagnostic enzyme kits, for the enzymatic production of sodium gluconate from glucose, for the neutralization of hydrogen peroxide waste, and for the removal of hydrogen peroxide and/or generation of oxygen in foods and beverages. In addition, bovine catalase has been the preferred enzyme for diagnostic purposes and for pharmaceutical related applications such as contact-lens cleansing and disinfection, and hydrogen peroxide neutralization). It is also known to topically apply a combination of a catalase containing composition and a hydrogen peroxide cream to the skin to produce oxygen and water, and to destroy peroxides using a combination of products commercially available under the tradename, Agera® of Biosyn, Inc., Harahan, La. However, the ability to use an encapsulated catalase in a sustained heat-generating topical composition has not heretofore been known.

The micrococcus catalase is preferably *Micrococcus lysate*, and it is present in the composition in an unencapsulated and an encapsulated form. The catalase component of the present invention has at least one encapsulated catalase. The encapsulated catalase is contained in a vesicle, also known as a microcapsule, using methodology disclosed in, for example, U.S. Pat. Nos. 5,395,620 and 5,811,114, the contents of which are incorporated herein by reference. In general, the encapsulation is done by combining a solution containing atelocollagen and a glycosaminoglycan in the presence of the catalase. Atelocollagen is a type of collagen from which the telopeptides which crosslink typical collagen have been removed. The use of glycosaminoglycans is well known in the art, and for the present invention, may be selected from, for example, chondroitin 4-sulfate, chondroitin 6-sulfate, dermatan sulfate, heparan sulfate, keratan sulfate, heparin, and derivatives thereof, preferably, the cosmetically or pharmaceutically acceptable salts, such as calcium or sodium salts are used, such as for example sodium chondroitin sulfate. Cross-linking reagents are useful in preparing the vesicles, and may include, but are not limited to silica dimethyl silylate. An encapsulated catalase suitable for use in the present invention is available commercially from Coletica, of Bioetica, Inc., Northport, N.Y. as CELA279A or B.

The encapsulated catalase is present in a heat-generating effective amount such that the catalase within the final vesicle is in the range of about 0.1 to 10 percent, and preferably about 1 to 6 percent by weight of the encapsulated catalase. The term "heat-generating effective amount" as used herein refers to an amount of encapsulated catalase in the catalase component that brings about a sustained release of heat as described above. Accordingly, the amount of encapsulated catalase suitable in the catalase component of the present invention is about 0.2 to about 8.0 percent, and preferably about 0.5 to about 5.0 percent by weight of the composition. The unencapsulated catalase is present in an amount of about 0.1 to about 4.0 percent, and preferably about 0.2 to about 2.0 percent by weight of the composition.

The encapsulated catalase of the present invention provides an unexpected sustained release of heat generated in the presence of the peroxide component. The amount of heat is not provided by a constant temperature, but rather, is supplied by a gradual and continual decrease in temperature over a period of time. Hydrogen peroxide, which has germ-killing, cleaning, bleaching and disinfecting activities is utilized widely to disinfect contact lenses and as a bleaching agent for textile materials and hair. However, hydrogen peroxide is known to generate free oxygen having high reactivity. The production of free oxygen radicals causes the denaturation of proteins. Therefore, the decomposition of hydrogen peroxide is important, especially on the skin. The use of catalases for this purpose is generally recognized as an efficient method for waste treatment, contact lens cleansing, and other applications, but it has not been recognized for modifying the heat curve and fine tuning the sensation of heat felt on the skin. Preferably, the peroxide component is a hydrogen peroxide, and more preferably it is urea hydrogen peroxide. The peroxide in the peroxide component is present in an amount of about 0.1 to 5.0 percent by weight of the peroxide component. The peroxide component can be applied as a separate solution or simultaneously with the catalase component.

In a preferred embodiment of the present invention, the sustained release of heat is enhanced by the addition of a non-catalase heat-generating agent in the catalase component comprising at least one heat generating agent other than catalase, unencapsulated (free) or encapsulated. The non-catalase heat-generating agent can include, for example, kaolin, magnesium sulfate, silica gel, iron powder, activated alumina, solid adsorbent materials capable of sorbing water exothermically that are known in the art, e.g., untreated, treated, or synthetic zeolite (alkali metal aluminosilicates, e.g., sodium silicoaluminate), and combinations thereof. The complementary non-catalase heat-generating agent may require the presence of a catalyst such as, for example, water. The combination of these other heat-generating agents permits the duration of heat to be extended, and therefore, the temperature-time curve and the sensation of heat on the skin to be further fine-tuned. In particular, the rate of heat released by exothermic reaction is modified to begin at an earlier time and/or to subside at a later time by combining the encapsulated catalase, the free catalase and the complementary heat-generating agents.

In yet another preferred embodiment of the present invention, the complementary heat-generating agent has at least two heat-generating agents. Preferably, at least one of the heat-generating agents in the complementary component is a zeolite, and more preferably the complementary agent contains a combination of untreated (i.e., unencapsulated) and treated (i.e., encapsulated) zeolite. Suitable untreated and treated zeolite is available commercially from Kobo Products, Inc., South Plainfield, N.J. The treated zeolite can, for example, be zeolite surface treated with about 3 percent isopropyl titanium triisostearate adsorbed onto the surface and available under the name Abscents SH1-54B from Kobo. This combination of heat-generating agents is beneficial because, while not wishing to be bound to any particular theory, the catalase reacts with hydrogen peroxide to produce water and oxygen as one source of heat, and the water from the first heat source is available potentially to react with the complementary heat generating agent to produce a second source of heat as a result of water adsorption.

The sequence of heat is believed to involve a release of heat by the free catalase (i.e., the unencapsulated catalase), the encapsulated catalase, the untreated and treated zeolite. The numerous effects of the present invention involving the encapsulated catalase can be achieved in any type of cosmetically or pharmaceutically acceptable vehicle for topical application with which the encapsulated catalase component and the additional complementary heat generating component are compatible, e.g., a gel, a cream, a lotion, an ointment, a mousse, a spray, a solid stick, a powder, a suspension, a dispersion, and the like. Preferably, however, the products are a massage cream or lotion for the body, especially as a spa products such as hand or foot massage products, body oils and products; shave cream and products; cleansers; masks; and a hair products such as scalp treatments, shampoos and conditioners.

The compositions of the present invention can be applied in two separate steps or simultaneously depending on the type of container used. The two reactive components can be dispensed from physically separate packages or from a unitary package with chambers. Examples of packages include, but are not limited to a pouch inside of a pouch, or a dual bladder system inside of a can. The components of either type of packages can be applied simultaneously or substantially simultaneously to the skin, where they commingle and react. The term "substantially simultaneously" as used herein refers to application of each of the components within temporal proximity to one another not longer than the stability of the initially applied component. In other words, there may be two steps to applying the two reactive components. In the first step, one component is applied to the skin and in the second step, the other component is applied over the first component within a period of time less than the stability time of the first component. The components are, thus, applied substantially simultaneously such that commingling occurs when the second component is applied on top of the first component. For example, one package can contain a cosmetic composition in the form of a moisturizer containing the catalase component which is applied to the skin. The other package can contain another cosmetic composition in the form of a foundation containing the peroxide component which is applied on top of the previously applied moisturizer. Commingling occurs when the foundation is applied over the layer of the moisturizer on the skin.

The compositions of the invention are applied to the skin in a manner appropriate to the intended desired end result in terms of heat generation. Preferably, a pea size of the catalase component is first applied to the skin. After the catalase component is rubbed onto the skin, a nickel size of the peroxide component is applied to the skin. The pea size is about 0.4 $cm^2$ on the skin, and the nickel size is about 4 $cm^2$ on the skin as these terms as known in the art. As a result, the catalase component and the peroxide component are applied in about a 10:1 ratio. Another benefit of the present invention is that the generation of heat can be re-activated by simply re-applying only the peroxide component to the area of the skin covered by the catalase component.

The other heat-generating agents are complementary with the encapsulated catalase in that the combined effect modifies the generation of heat by exothermic reaction such that the sensation of heat felt on the skin is stable and long-lasting. The present invention also relates to a method of exfoliating and softening the skin by applying to the skin the compositions containing the encapsulated catalase as these benefits are known in relation to catalase but not with respect to encapsulated catalase or encapsulated catalase in combination with other heat-generating agents. In another embodiment, application of the compositions of the present invention also reduces skin flakiness.

The invention is further illustrated by the following non-limiting examples:

EXAMPLE I

The following is a composition according to the present invention:

| Catalase Base | |
| --- | --- |
| Glycerin | 45.0 |
| Methyl gluceth-20 | 4.0 |
| Glycereth-26 | 1.0 |
| Free catalase | 1.0 |
| Encapsulated catalase | 2.0 |
| Zeolite | 5.0 |
| Treated zeolite | 2.0 |
| Keltrol (1% solution) | 39.0 |
| Methyl paraben | 0.5 |
| Imidazolidinyl urea | 0.5 |

| Urea Peroxide Phase | |
| --- | --- |
| Cetyl alcohol | 2.0 |
| Glyceryl stearate/PEG-100 Stearate | 8.0 |
| Cetearyl alcohol | 1.0 |
| Triglycerides | 8.0 |
| Dimethicone | 0.5 |
| Polysorbate 40 | 1.0 |
| Sorbitan palmitate | 0.5 |
| Water | 60.9 |
| Butylene glycol | 5.0 |
| Trisodium EDTA | 0.1 |
| Caprylyl glycol | 1.0 |
| Urea hydrogen peroxide | 12.0 |

EXAMPLE II

This example illustrates the ability of the compositions of the present invention to produce a linear change in temperature over time on the skin surface demonstrating a sustained release of heat. A comparative study is made with several products using known heat generating agents. Composition 1, Biore® Self-Heating Mask, uses a combination of butylene glycol, sodium silicoaluminate, and kaolin. Composition 2, Cosmence Masque Sauna, contains a combination of glycerin and kaolin. Composition 3, Avon Deep Cleansing Warming Mask, has a combination of dipropylene glycol, magnesium sulfate and kaolin. The compositions of the present invention are prepared according to Example I above and are tested twice.

The temperature of the bare skin is taken for a baseline measurement using a digital thermocouple applied to the surface of the skin using a circular motion to account for variations in the skin temperature in pea-size area on the skin. Each of the compositions is applied according to the directions on the product package and the temperature of the skin is measured using a digital thermocouple applied to the surface of the skin in a circular motion to account for "hot spots" on the skin.

The results demonstrate that the temperature of the skin using the compositions of the present invention is greater than about 35° C., about 39° C. for both samples, at the 30 second interval after application, and the percent difference in temperature per minute based on the initial baseline skin temperature for the compositions of the present invention gradually decreases during each of the first 3 minutes after application (i.e., −7.69 and −10.26 for the 1 minute interval, −11.11 and −5.71 for the 2 about 35° C. or less at the 30 second interval after application, and the percent difference in temperature per minute based on the initial baseline skin temperature, for each of the first 3 minutes after application is as follows. Composition 1 has a percent difference per minute of 0.00 at the 1 and 2 minute intervals, and −5.71 at the 3 minute interval; Composition 2 is 3.23 at the 1 minute interval, −1.56 at the 2 minute interval, and −1.59 at the 3 minute interval; and Composition 3 is 3.13 at the 1 minute interval, 0.00 at the 2 minute interval, and −3.03 at the 3 minute interval.

EXAMPLE III

A single blinded study is conducted to determine the rate and amount of heat on the skin upon topical application of the compositions of the present invention. A panel of ten woman are used in the study and they are free of a systemic illness, dermatological disorders in areas to be used in the study, are not pregnant and do not use systemic or topical retinoids, antihistamines or similar agents. The panelists are instructed to not wear moisturizer during the study. Each of the panelists apply a pea size amount of the catalase component of the present invention to their inner forearm followed by a nickel size amount of the peroxide phase of the present invention on top of it. After 2 minutes, the components of the present invention are rinsed off with cool water. The panelists are given a questionnaire regarding various attributes of the heat-generating composition of the present invention, such as redness, itchiness, stinging, and overall product performance. All of the panelists respond that they experience no stinging, 90% percent of the panelists report that the did not experience redness or itchiness. The rate of heat is apparently is achieved without stinging and substantially without redness or itchiness.

What is claimed is:

1. A heat-generating composition for topical application to the skin comprising at least one unencapsulated heat-generating agent comprising a catalase agent or a non-catalase agent and at least one encapsulated catalase, and a peroxide component.

2. The composition of claim 1 having a protracted decrease in temperature for a period of about 3 minutes after the composition is applied to the skin.

3. The composition of claim 2 wherein the decrease in temperature is at least about 2° C. in a period of about 5 minutes after the composition is applied to the skin.

4. The composition of claim 1 in which the encapsulated catalase is present in an amount of from about 0.2 to about 8.0 percent by weight of the composition.

5. The composition of claim 4 in which the encapsulated catalase is present in an amount of from about 1.0 to about 5.0 percent by weight of the composition.

6. The composition of claim 1 wherein the unencapsulated non-catalase agent is selected from the group consisting of zeolite, kaolin, magnesium sulfate, silica gel, iron powder, and activated alumina.

7. The composition of claim 6 in which the unencapsulated non-catalase agent is zeolite.

8. The composition of claim 7 further comprising an encapsulated zeolite.

9. The composition of claim 1 in which the unencapsulated catalase is present in an amount of about 0.1 to about 4.0 percent.

* * * * *